(12) United States Patent
Tower et al.

(10) Patent No.: US 12,396,792 B2
(45) Date of Patent: Aug. 26, 2025

(54) NEPHROSCOPE WITH FLEXIBLE AND ARTICULATABLE DISTAL PORTION

(71) Applicant: GYRUS ACMI, INC., Southborough, MA (US)

(72) Inventors: Connor Tower, Hudson, MA (US); Jessica N. Stem, Coon Rapids, MN (US)

(73) Assignee: Gyrus ACMI, Inc., Westborough, MA (US)

(*) Notice: Subject to any disclaimer, the term of this patent is extended or adjusted under 35 U.S.C. 154(b) by 744 days.

(21) Appl. No.: 17/162,317

(22) Filed: Jan. 29, 2021

(65) Prior Publication Data

US 2021/0236204 A1 Aug. 5, 2021

Related U.S. Application Data

(60) Provisional application No. 62/968,360, filed on Jan. 31, 2020.

(51) Int. Cl.
*A61B 18/22* (2006.01)
*A61B 1/00* (2006.01)
(Continued)

(52) U.S. Cl.
CPC .......... *A61B 18/22* (2013.01); *A61B 1/00066* (2013.01); *A61B 1/00087* (2013.01);
(Continued)

(58) Field of Classification Search
CPC ............ A61B 1/00066; A61B 1/00087; A61B 1/0051; A61B 1/0057; A61B 1/012;
(Continued)

(56) References Cited

U.S. PATENT DOCUMENTS 4,802,461 A 2/1989 Cho
2007/0225556 A1* 9/2007 Ortiz .................... A61B 1/0684
600/172
(Continued)

FOREIGN PATENT DOCUMENTS

CN 101040775 A 9/2007
CN 108601622 A 9/2018
(Continued)

OTHER PUBLICATIONS

"European Application Serial No. 21154436.6, Response filed Jan. 25, 2022 to Extended European Search Report mailed Jun. 23, 2021", 8 pgs.
(Continued)

*Primary Examiner* — Amanda K Hulbert
(74) *Attorney, Agent, or Firm* — Schwegman Lundberg & Woessner, P.A.

(57) ABSTRACT

A nephroscope can include a body that is at least partially insertable into a kidney of a patient. An articulation controller on a grippable proximal portion of the body can adjust a position of a flexible distal portion of the body to locate a kidney stone when the body is inserted into the kidney of the patient. The articulation controller can optionally releasably lock the articulation of the flexible distal portion, to fixedly position the flexible distal portion at a specified location proximate the kidney stone. The distal end of the body can include an illuminator to illuminate the kidney stone, a camera to provide a video image of the illuminated kidney stone, an optical fiber to deliver laser light that ablates the kidney stone, and an irrigation lumen and a suction lumen to flush the kidney stone and remove kidney stone fragments.

18 Claims, 9 Drawing Sheets

(51) Int. Cl.
*A61B 1/005* (2006.01)
*A61B 1/04* (2006.01)
*A61B 1/06* (2006.01)
*A61B 18/24* (2006.01)
*A61B 18/00* (2006.01)

(52) U.S. Cl.
CPC .............. *A61B 1/0057* (2013.01); *A61B 1/04* (2013.01); *A61B 1/0684* (2013.01); *A61B 18/245* (2013.01); *A61B 2018/00511* (2013.01); *A61B 2018/00577* (2013.01); *A61B 2018/2253* (2017.05); *A61B 2218/002* (2013.01); *A61B 2218/007* (2013.01)

(58) Field of Classification Search
CPC ......... A61B 1/04; A61B 1/0684; A61B 1/307; A61B 18/22; A61B 18/245; A61B 18/26; A61B 2018/00511; A61B 2018/00577; A61B 2018/2253; A61B 2218/002; A61B 2218/007
See application file for complete search history.

(56) References Cited

U.S. PATENT DOCUMENTS

| | | | | |
|---|---|---|---|---|
| 2013/0211415 | A1* | 8/2013 | Zerfas | A61B 17/221 606/1 |
| 2016/0073855 | A1* | 3/2016 | Farr | A61B 1/0676 600/109 |
| 2017/0215965 | A1* | 8/2017 | Harrah | A61B 1/018 |

FOREIGN PATENT DOCUMENTS

| | | |
|---|---|---|
| CN | 109843144 A | 6/2019 |
| CN | 113197540 A | 8/2021 |
| JP | 2000189380 A | 7/2000 |
| JP | 2002272677 A | 9/2002 |
| JP | 2005160790 A | 6/2005 |
| JP | 2007532279 A | 11/2007 |
| JP | 2008526360 A | 7/2008 |
| JP | 2012509720 A | 4/2012 |
| JP | 2017094082 A | 6/2017 |
| JP | 2018505703 A | 3/2018 |
| JP | 2018143539 A | 9/2018 |
| JP | 2018143653 A | 9/2018 |
| JP | 2019536522 A | 12/2019 |
| JP | 2021122740 | 8/2021 |
| WO | 2004096026 | 11/2004 |
| WO | WO-2019003586 A1 | 1/2019 |
| WO | 2021026142 | 2/2021 |
| WO | 2021242853 | 12/2021 |

OTHER PUBLICATIONS

"European Application Serial No. 21154436.6, Communication Pursuant to Article 94(3) EPC mailed Jul. 26, 2023", 4 pgs.

"How Endoscopes Work", Published on Feb. 13, 2015 by admin Filed under Gastroenterology and Hepatology Last modified Feb. 13, 2015, (Feb. 13, 2015), 15 pgs.

"European Application Serial No. 21154436.6, Extended European Search Report mailed Jun. 23, 2021", 6 pgs.

"European Application Serial No. 21154436.6, Response filed Nov. 30, 2023 to Communication Pursuant to Article 94(3) EPC mailed Jul. 26, 2023", w/ claims, 11 pgs.

"Japanese Application Serial No. 2021-014611, Notification of Reasons for Refusal mailed Aug. 13, 2024", w/ English translation, 14 pgs.

"Japanese Application Serial No. 2021-014611, Response filed Oct. 8, 2024 to Notification of Reasons for Refusal mailed Aug. 13, 2024", w/ english claims, 9 pgs.

"Chinese Application Serial No. 202110136151.X, Office Action mailed Feb. 26, 2025", W/English Translation, 18 pgs.

"Japanese Application Serial No. 2021-014611, Notification of Reasons for Refusal mailed Nov. 26, 2024", w English Translation, 8 pgs.

"European Application Serial No. 21154436.6, Communication Pursuant to Article 94(3) EPC mailed May 9, 2025", 4 pgs.

"Japanese Application Serial No. 2021-014611, Response filed Apr. 25, 2025 to Notification of Reasons for Refusal mailed Nov. 26, 2024", w english claims, 12 pgs.

\* cited by examiner

NEPHROSCOPE WITH FLEXIBLE AND ARTICULATABLE DISTAL PORTION

CROSS REFERENCE TO RELATED APPLICATION

This patent application claims the benefit of U.S. Provisional Patent Application No. 62/968,360, filed Jan. 31, 2020, which is incorporated by reference herein in its entirety.

FIELD OF THE DISCLOSURE

The present disclosure relates generally to a device associated with a medical procedure to remove kidney stones.

BACKGROUND OF THE DISCLOSURE

A medical procedure referred to as percutaneous nephrolithotomy (PCNL) can be used to remove kidney stones, particularly stones that are relatively large, firm, resistant to other forms of stone treatment, or any combination thereof. A nephroscope is a viewing device, such as for viewing a kidney stone or other object within a region of a kidney.

SUMMARY

In an example, a nephroscope can include a body at least partially insertable into a kidney of a patient. The body can include a grippable proximal portion, an elongated rigid portion extending from the grippable proximal portion, and a flexible distal portion extending distally from the elongated rigid portion to a distal end. The nephroscope can include an articulation controller on the grippable proximal portion of the body. The articulation controller can adjust a position of the flexible distal portion to locate a kidney stone when the body is inserted into the kidney of the patient. The distal end of the body can further illuminate the kidney stone, provide a video image of the illuminated kidney stone, ablate the kidney stone, and remove kidney stone fragments.

In an example, a nephroscope can include a body partially insertable into a kidney of a patient. The body can include a grippable proximal portion, an elongated rigid portion extending from the grippable proximal portion, and a flexible distal portion extending distally from the elongated rigid portion to a distal end. The nephroscope can include an articulation controller located on the grippable proximal portion of the body. The articulation controller can adjust a position of the flexible distal portion to locate a kidney stone when the body is inserted into the kidney of the patient. The distal end of the body can further illuminate the kidney stone, provide a video image of the illuminated kidney stone, and deliver laser light to the kidney stone to ablate the kidney stone into kidney stone fragments. The distal end of the body can further irrigate the kidney stone and the kidney stone fragments with irrigation fluid and remove the irrigation fluid and the kidney stone fragments.

In an example, a nephroscope can include a body partially insertable into a kidney of a patient. The body can include a grippable proximal portion, an elongated rigid portion extending from the grippable proximal portion, and a flexible distal portion extending distally from the elongated rigid portion to a distal end. The nephroscope can include a plurality of pull wires that extend along the body to the flexible distal portion. The pull wires can be located at a respective plurality of angular locations on the body and on the flexible distal portion. The nephroscope can include an articulation controller located on the grippable proximal portion of the body. The articulation controller can adjust the position of the flexible distal portion by controllably applying a proximally oriented force to a first pull wire, of the plurality of pull wires, at a first angular location to cause the flexible distal portion of the body to move radially in the direction of the first angular location. The plurality of pull wires and the articulation controller can adjust a position of the flexible distal portion to locate a kidney stone when the body is inserted into the kidney of the patient. The nephroscope can include a circuit board located on the distal end of the body. The nephroscope can include at least one light-emitting diode on the circuit board. The at least one light-emitting diode can emit light distally away from the distal end of the body to illuminate the kidney stone. The nephroscope can include a camera on the circuit board. The camera can capture a video image of the illuminated kidney stone. The nephroscope can include an optical fiber extending along a working channel in the body to the distal end of the body. The optical fiber can deliver laser light to the kidney stone to ablate the kidney stone into kidney stone fragments. The nephroscope can include an irrigation lumen extending along the body to the distal end of the body. The irrigation lumen can deliver an irrigation fluid to the kidney stone and the kidney stone fragments. The nephroscope can include a suction lumen extending along the body to the distal end of the body. The suction lumen can remove the irrigation fluid and the kidney stone fragments from the kidney.

BRIEF DESCRIPTION OF THE DRAWINGS

Corresponding reference characters indicate corresponding parts throughout the several views. Elements in the drawings are not necessarily drawn to scale. The configurations shown in the drawings are merely examples and should not be construed as limiting in any manner.

DETAILED DESCRIPTION

Figure 1:
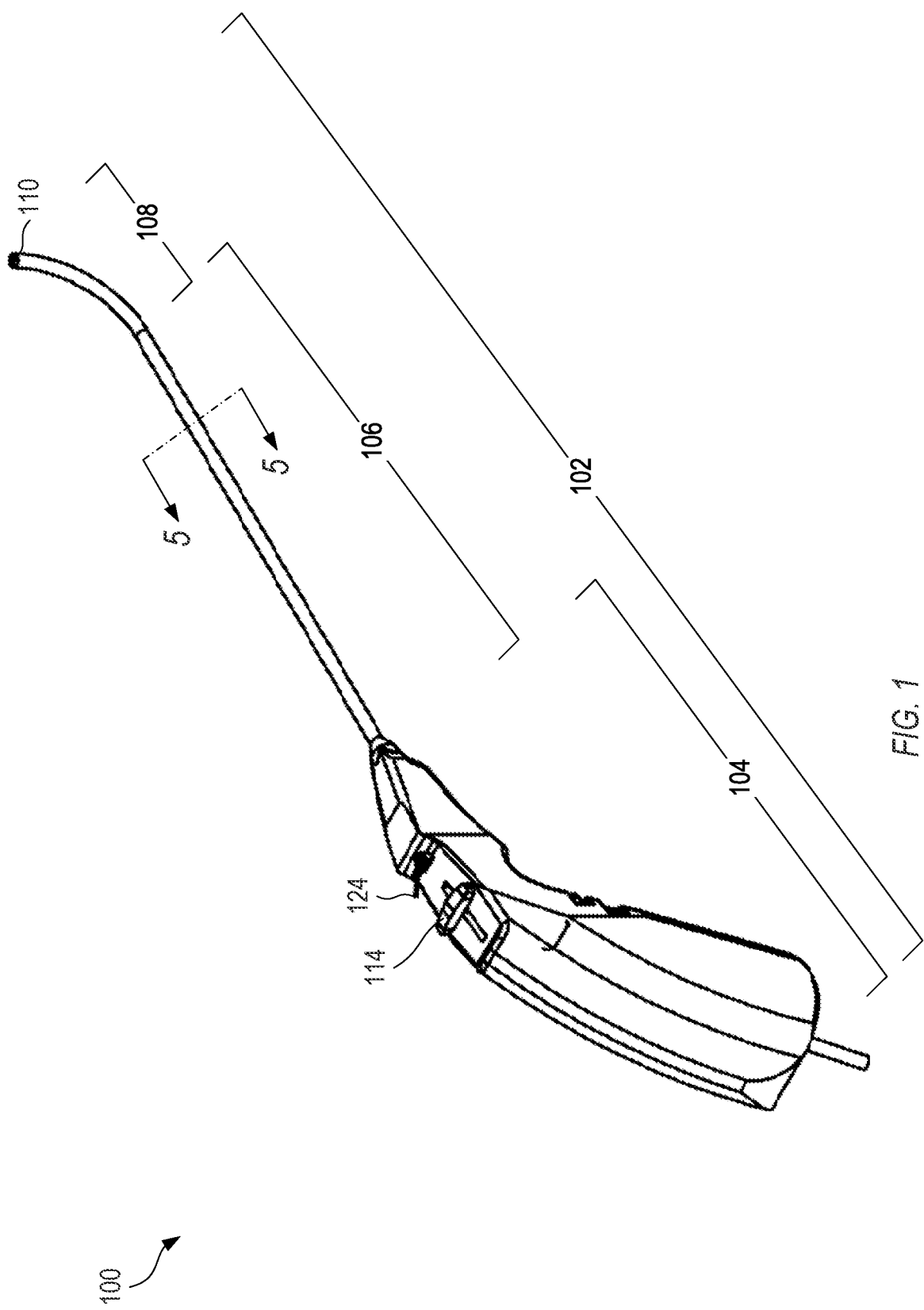
FIG. 1 shows a perspective view of an example of a nephroscope having a flexible distal portion.

The medical procedure referred to as percutaneous nephrolithotomy (PCNL) can be used to remove kidney stones, particularly stones that are relatively large, firm, resistant to other forms of stone treatment, or any combination thereof. In PCNL, a practitioner can insert a rigid scope through an incision in a patient's back and into the patient's kidney. Through the scope, the practitioner can locate the kidney stones, break the kidney stones into smaller fragments, and withdraw the stone fragments from the kidney. The scope can include an endoscope, a nephroscope, and/or a cystoscope.

In some procedures, the practitioner can break the stone into smaller fragments by applying a mechanical force, such as an oscillating force, to the stone, such as by applying a pulse with variable amplitudes and/or frequencies that originates outside the patient's body or using an ultrasonic lithotripter to apply an oscillating force, similar to the operation of a jack hammer. Once the stones have been broken into relatively small fragments, the practitioner can extract the small fragments through the scope.

Additionally or alternatively, the practitioner can break the stones into smaller fragments by illuminating the stone, through the scope, with relatively high-powered infrared laser light. The laser light can ablate a kidney stone into smaller fragments.

In some procedures, the practitioner may use one instrument for breaking the stone into smaller fragments and another, separate, instrument for visually examining other areas of the kidney. For example, a practitioner can use a rigid nephroscope to deliver the oscillating (or pulsatile) force. The rigid nephroscope can have limited viewing capabilities, so that the practitioner can see a relatively small area near a location of the jack-hammer oscillating force but cannot see anything located away from the small area. To view other portions of the kidney, the practitioner can withdraw the rigid nephroscope, and then use a flexible cystoscope to visually examine other areas of the kidney, such as to help ensure that the practitioner has accounted for and removed all of the fragments of the kidney stone. If the practitioner did miss a piece of the stone, the practitioner can then withdraw the flexible cystoscope, reinsert the rigid nephroscope to retrieve the missed piece of the stone, and reinsert the flexible cystoscope to repeat the visual examination of the other areas of the kidney.

There are drawbacks to using multiple instruments in such procedures. For example, it is time-consuming to repeatedly withdraw one instrument and insert another. In addition, it is relatively expensive to sterilize the flexible cystoscope for later surgeries.

As an improvement over such procedures, which use one instrument to break the stone into smaller fragments and another instrument to investigate other areas of the kidney, the nephroscope described herein can combine the functions of these two separate instruments into a single device. In addition to saving the practitioner time that would otherwise be spent swapping instruments, the nephroscope described herein can be configured for single-use, which can reduce costs associated with sterilizing a reusable flexible cystoscope.

For example, a nephroscope can include a body at least partially insertable into a kidney of a patient. The body can include a grippable proximal portion, an elongated rigid portion extending from the grippable proximal portion, and a flexible distal portion extending distally from the elongated rigid portion to a distal end. The nephroscope can include an articulation controller on the grippable proximal portion of the body. The articulation controller can adjust a position of the flexible distal portion to locate a kidney stone when the body is inserted into the kidney of the patient. The articulation controller can optionally releasably lock the articulation of the flexible distal portion, to fixedly position the flexible distal portion at a specified location proximate the kidney stone. The distal end of the body can illuminate the kidney stone, provide a video image of the illuminated kidney stone, ablate the kidney stone, and remove kidney stone fragments.

Figure 2:
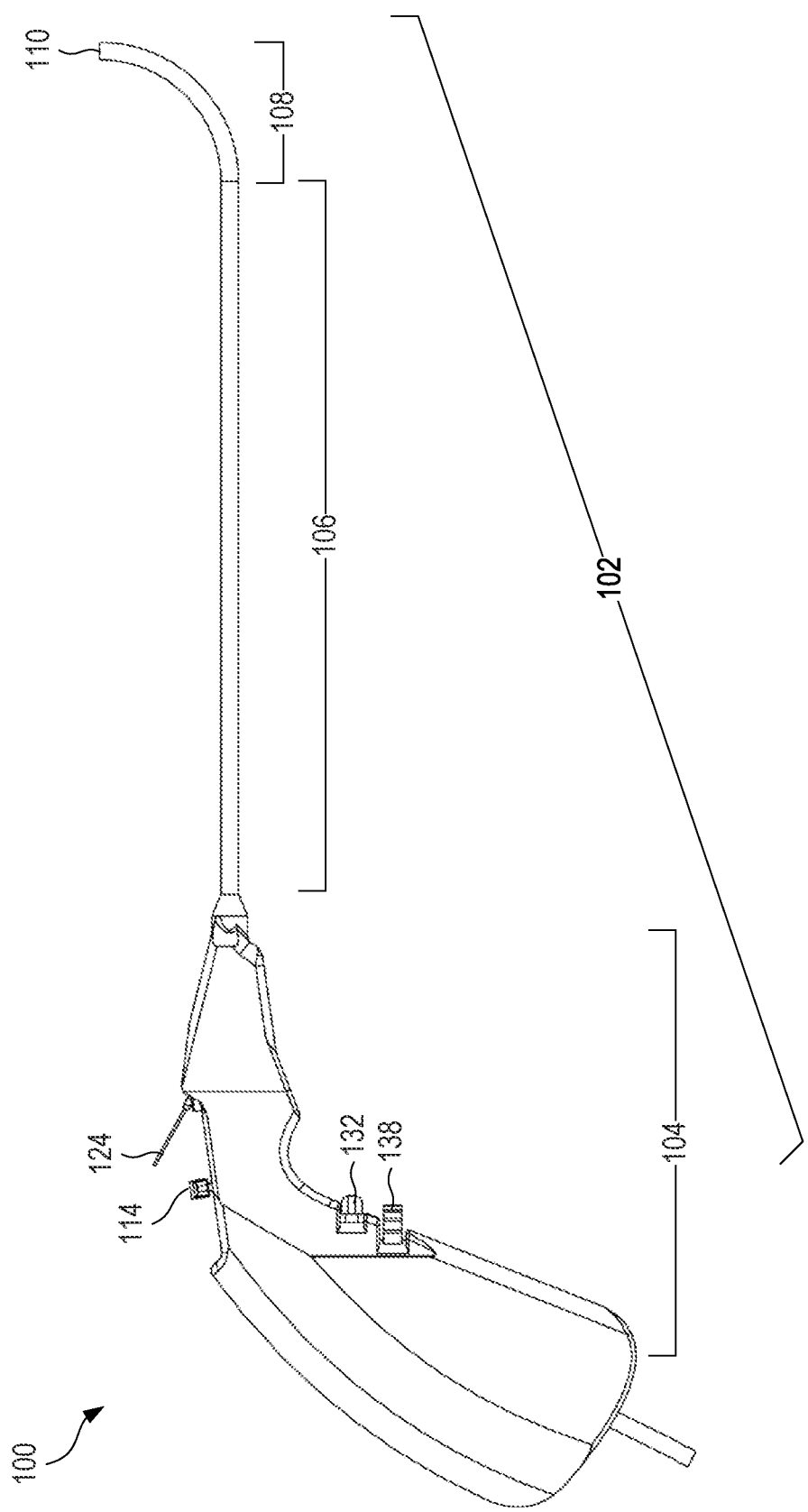
FIG. 2 shows a side view of the nephroscope of FIG. 1.
Figure 3:
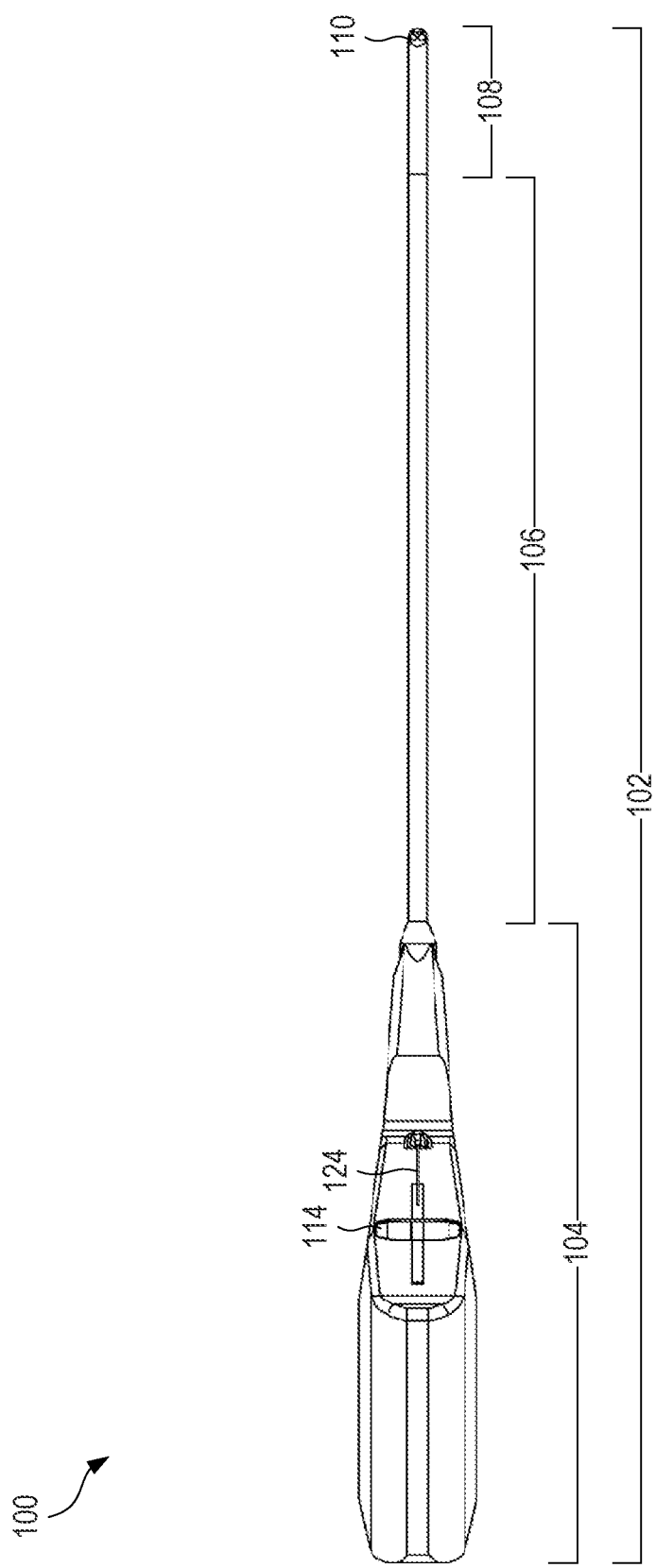
FIG. 3 shows a top view of the nephroscope of FIG. 1.
Figure 4:
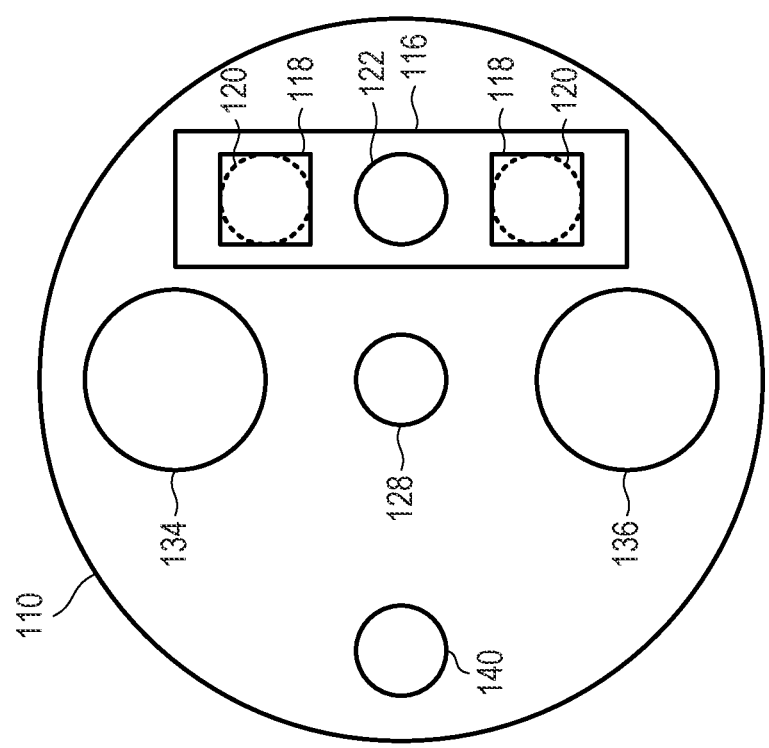
FIG. 4 shows an end-on view of the distal tip of the nephroscope of FIG. 1.
Figure 5:
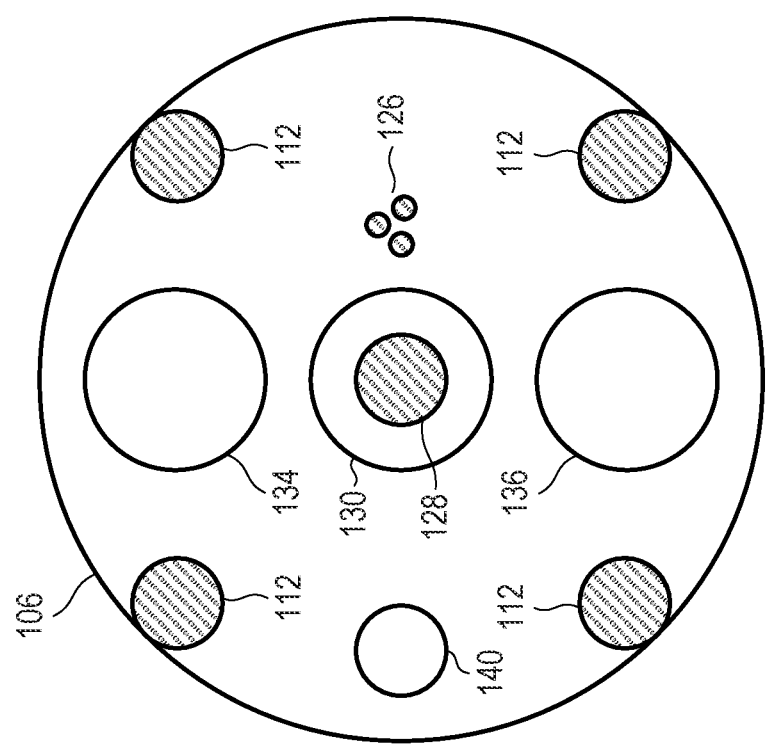
FIG. 5 shows a cross-sectional view of the elongated rigid portion of the nephroscope of FIG. 1.

FIG. 1 shows a perspective view of an example of a nephroscope 100 having a flexible distal portion. FIG. 2 shows a side view of the nephroscope 100 of FIG. 1. FIG. 3 shows a top view of the nephroscope 100 of FIG. 1. FIG. 4 shows an end-on view of the distal tip of the nephroscope 100 of FIG. 1. FIG. 5 shows a cross-sectional view of the elongated rigid portion of the nephroscope 100 of FIG. 1. The nephroscope 100 of FIGS. 1-5 is but one example of a nephroscope 100; other suitable configurations can also be used.

The nephroscope 100 can include a body 102 that is at least partially insertable into a kidney of a patient. The body 102 can include a handle, a hub, or other grippable proximal portion 104. The grippable proximal portion 104 can be formed from plastic, metal, or any other suitable material.

The body 102 can include an elongated rigid portion 106 extending from the grippable proximal portion 104. The elongated rigid portion 106 can be formed from plastic, metal, and/or any other suitable material. For example, the elongated rigid portion 106 can include a polymer outer portion that surrounds a stainless steel wire mesh, which in turn surrounds additional components of the nephroscope 100 that are described in detail below. The elongated rigid portion 106 can remain rigid, relative to the grippable proximal portion 104, when the practitioner inserts the nephroscope 100 into the body of the patient, and when the practitioner passes one or more stone-fragmenting instruments, such as an ultrasonic lithotripter, through the nephroscope 100.

The body 102 can include a flexible distal portion 108 extending distally from the elongated rigid portion 106 to a distal end 110. The flexible distal portion 108 can be more flexible than the elongated rigid portion 106. For example, the flexible distal portion 108 can include a series of rigid rings, each ring connected to the adjacent rings by a respective joint that includes a pivot pin, each pivot pin being circumferentially offset from an adjacent pin by 90 degrees. The pins and rings can form a manipulatable structure that can curl in any direction.

One or more pull wires 112 (see FIG. 5) can extend along the body 102 to the flexible distal portion 108. The pull wires 112 can control the curl of the flexible distal portion 108. The pull wires 112 can be located at a respective plurality of angular locations on the body 102 and on the flexible distal portion 108. For examples in which the body 102 has one or more portions that have a circular cross-section, the angular locations can correspond to circumferential locations around the circular cross-section of the body 102. As a specific example in FIG. 5, there are four pull wires 112 positioned at angular locations of 45 degrees, 135 degrees, 225 degrees, and 315 degrees, with respect to a horizontal axis (or a vertical axis) in FIG. 5. Other numbers of pull wires and other angular locations can also be used.

An articulation controller 114 can be located on the grippable proximal portion 104 of the body 102. The articulation controller 114 can be located to be actuatable by a thumb of the human hand when the human hand grips the grippable proximal portion 104 of the body 102. The articulation controller 114 can adjust the position of the flexible distal portion 108. The articulation controller 114 can adjust the position by controllably applying a proximally oriented force to a first pull wire 112, where the first pull wire 112 is located at a first angular location. The proximally oriented force can cause the flexible distal portion 108 of the body 102 to move radially in the direction of the first angular location. The pull wires 112 and the articulation controller 114 can adjust a position of the flexible distal portion 108 to locate a kidney stone when the body 102 is inserted into the kidney of the patient.

In a specific example, the nephroscope 100 can include four pull wires 112 positioned at angular locations of 45 degrees, 135 degrees, 225 degrees, and 315 degrees, with respect to a horizontal axis (or a vertical axis) in FIG. 5. In this specific example, the pull wires 112 at 45 degrees and 225 degrees are joined together around a first gear in the grippable proximal portion 104, and the pull wires 112 at 135 degrees and 315 degrees are joined together around a second gear in the grippable proximal portion 104. In this specific example, the articulation controller 114 can include a first knob coupled to the first gear, which can controllably pull on one of the pull wires 112 at 45 degrees and 225 degrees and push on the other of the pull wires 112 at 45 degrees and 225 degrees. Similarly, the articulation controller 114 can include a second knob coupled to the second gear, which can controllably pull on one of the pull wires 112 at 135 degrees and 315 degrees and push on the other of the pull wires 112 at 135 degrees and 315 degrees.

Once a practitioner has located a stone, the practitioner can use the articulation controller 114, or another suitable element, to lock the articulation of the flexible distal portion 108. For example, the articulation controller 114, or other suitable element, can removably force the pull wires 112 against one or more fixed elements in the grippable proximal portion 104 of the body 102, thereby locking the pull wires 112 in place, and in turn locking a position of the flexible distal portion 108. Other suitable locking mechanisms can also be used. The articular controller 114 can deploy the locking mechanism via a button, a lever, a slider, a switch, a dial, or another suitable deployment mechanism. With the articulation being locked, the practitioner can deploy a lithotripter as needed. This locking of the articulation of the flexible distal portion 108 can be referred to as the flexible distal portion 108 being selectively flexible.

The articulation controller 114, or other suitable element, can also unlock the articulation of the flexible distal portion 108. For example, the articulation controller 114, or other suitable element, can release the pull wires 112 from the one or more fixed elements in the grippable proximal portion 104 of the body 102. The articular controller 114 can use the locking mechanism to deploy the unlocking mechanism. For example, the locking mechanism can involve depressing a button, and the unlocking mechanism can involve releasing or pulling the button. The articular controller can 114 can use a separate button, lever, slider, switch, dial, or another suitable deployment mechanism to unlock the articulation of the flexible distal portion 108. With the articulation being unlocked, the practitioner can reposition the flexible distal portion 108 as needed to inspect additional portions of the kidney. Other locking and/or unlocking mechanisms can also be used. The articular controller 114 can switch between a first configuration, in which the position of the flexible distal portion 108 is adjustable, and a second configuration, in which the position of the flexible distal portion 108 is lockable at a selectable position. This is but one example of a configuration for the pull wires 112 and the articulation controller 114; other configurations can also be used.

The flexible distal portion 108 can be flexible relative to the handle or the elongated rigid portion 106 once inside the kidney and during imaging. The flexible distal portion 108 can have sufficient columnar strength to ensure that it can be inserted through the puncture. The flexible distal portion 108 can be constructed similar to flexible endoscopes. The flexible distal portion 108 can include a torque carrier and additional supporting structures, such as a braid or a mesh, that can help provide columnar strength and can help increase pushability, but may still be flexible relative to the elongated rigid portion 106. The articulation controller 114 can control the articulation of the flexible distal portion 108 so that the flexible distal portion 108 can be rigid (with a comparable rigidity to the elongated rigid portion 106) during insertion through the puncture into the kidney, and may be actuated to adjust the rigidity so that the flexible distal portion 108 can be distally moved and imaged once inside the kidney. Once the stone is located, the articulation controller 114 can be actuated again so that flexible distal portion 108 can have sufficient rigidity and its articulation is locked. The flexible distal portion 108 can therefore be stationary relative to the elongated rigid portion 106 and not move any further, during stone ablation. After ablation, the practitioner can further articulate the flexible distal portion 108 to do further imaging.

A substrate 116 (see FIG. 4) can be located on the distal end 110 of the body 102. The substrate 116 can include one or more of a circuit board, a hybrid chip, a ceramic component, or other suitable components or elements. The substrate 116, and any components located on the substrate 116, can be formed separately from the body 102 and can be subsequently attached to the distal end 110 of the body 102. The substrate 116, and any components located on the substrate 116, can be formed integrally with the distal end 110 of the body 102. The substrate 116 can be formed integrally with the distal end 110 of the body 102, and any components located on the substrate 116 can be subsequently attached to the substrate 116.

To visualize the kidney stone fragments, the nephroscope 100 can include a visualization system at the distal end 110 of the body 102. The visualization system can illuminate a working area of the kidney stone and can generate a video image or one or more static images of the illuminated area of the kidney stone.

Figure 6:
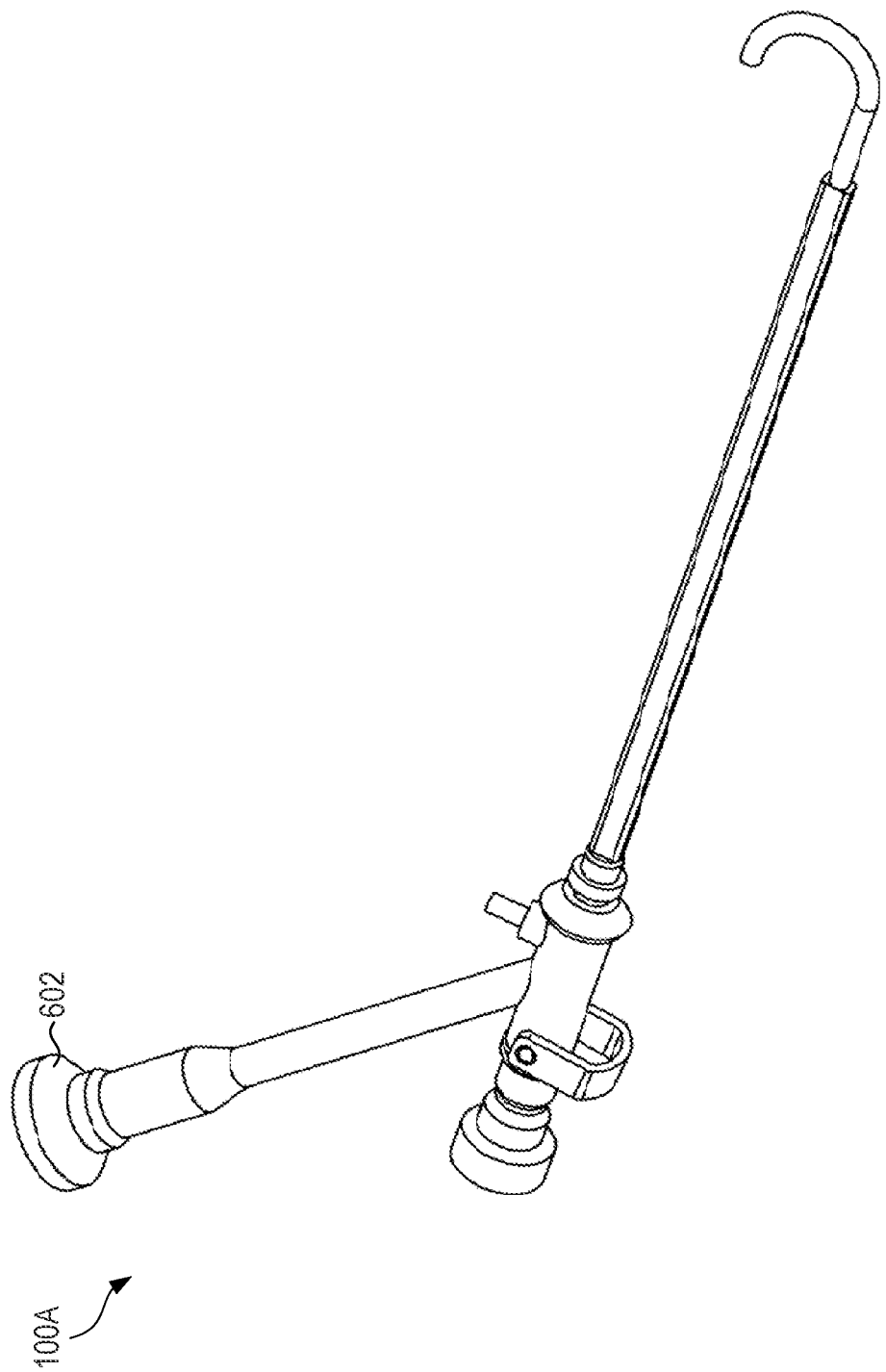
FIG. 6 shows a perspective view of an example of a nephroscope having a flexible distal portion, and having a video monitor that is attached to or formed integrally with the nephroscope.

FIG. 6 shows a perspective view of an example of a nephroscope 100A having a flexible distal portion, and having a video monitor 602 that is attached to or formed integrally with the nephroscope 100A. The visualization system can direct the video image to a display, such as the video monitor 602. The display can be external to the nephroscope 100 and can be viewable during the kidney stone removal procedure. The video monitor 602 can be used with any or all of the elements of the nephroscope 100 of FIGS. 1-5.

Returning to FIGS. 1-5, the visualization system can include at least one light-emitting diode 118 (see FIG. 4) located on the substrate 116. The substrate 116 can be a circuit board that mechanically supports and electrically powers each light-emitting diode 118. The light-emitting diode or diodes 118 can emit light distally away from the distal end 110 of the body 102 to illuminate the kidney stone. One or more light-emitting diodes 118 can emit white light to illuminate the kidney stone. White light can allow the practitioner to observe discolorations or other color-based effects on the kidney stones or on the tissue proximate the distal end 110 of the body 102. One or more light-emitting diodes 118 can emit blue light to illuminate the kidney stone. Blue light can be well-suited to show thermal tissue spread and thereby detect damage in the tissue. Other colors and/or color bands, such as red, amber, yellow, green, or others, can also be used.

The substrate 116 can include an optional lens 120 (see FIG. 4) for each light-emitting diode 118, which can angularly adjust the light output from the light-emitting diode 118. The lens 120 can narrow the light output from the light-emitting diode 118. The lens 120 can widen the light output from the light-emitting diode 118. Such an angular adjustment can help ensure that the kidney stones and the tissue are sufficiently illuminated within a specified angular field of view.

The visualization system can include a camera 122 (see FIG. 4) located on the substrate 116. The substrate 116 can be a circuit board that mechanically supports and electrically powers the camera 122. The camera 122 can capture a video image or one or more static images of the illuminated kidney stone. The video image can be in real-time, or nearly real-time with a relatively short latency for processing, so that the practitioner can observe the kidney stone and the surrounding tissue as the practitioner manipulates the body 102 and controls of the nephroscope 100. The camera 122 can include a lens and a multi-pixel sensor located at a focal plane of the lens. The sensor can be a color sensor, such as a sensor that provides intensity values for red light, green light, and blue light for each pixel in the video image. The circuit board can produce a digital video signal representing the captured video image of the illuminated kidney stone. The digital video signal can have a video refresh rate of 10 Hz, 20 Hz, 24 Hz, 25 Hz, 30 Hz, 40 Hz, 50 Hz, 60 Hz, or another suitable video refresh rate.

The at least one light-emitting diode 118 can include two light-emitting diodes 118. The camera 122 can be located between the two light-emitting diodes 118. The at least one light-emitting diode 118 can include multiple light-emitting diodes 118 that surround the camera 122. Each of the multiple light-emitting diodes 118 can emit the same color band or different color bands. For example, one light-emitting diode of the multiple light emitting diodes 118 can emit white light and another can emit blue light. The different light sources can be used to better visualize different elements within the body, such as a kidney stone or tissue, as described above. These orientations of the light-emitting diodes 118 and the camera 122 can be beneficial in that the illumination can be relatively uniform over the field of view of the camera 122 (e.g., the illumination may have relatively little bias toward one side of the field of view).

The visualization system can include an electrical port 124 on the body 102 and coupled to the substrate 116, such as the circuit board. For example, one or more wires 126 can extend along the body 102 from the electrical port 124 to the substrate 116. The electrical port 124 can receive electrical power to power the circuit board. The electrical port 124 can provide a wired connection to the digital video signal via a suitable, optionally multi-pin, electrical connector. The substrate 116, such as the circuit board, can communicate the digital video signal wirelessly to a display device that is external to the nephroscope 100, such as a user device, a display, a computer monitor, a heads-up display, a wearable display, a virtual reality display, an augmented reality display, and others.

An optical fiber 128 (see FIG. 5) can extend along a working channel 130 (see FIG. 5) in the body 102 to the distal end 110 of the body 102. The optical fiber 128 can deliver laser light to the kidney stone to ablate the kidney stone into kidney stone fragments.

In some examples, the optical fiber 128 can be integrated into the nephroscope 100. For example, the optical fiber 128 can be shipped with the nephroscope 100, and/or can remain with the nephroscope 100 after use. In some examples, the optical fiber 128 can be separate from the nephroscope 100. For example, the optical fiber 128 can be fed along a working channel of the nephroscope 100 prior to use, and/or retrieved from a working channel of the nephroscope 100 after use.

A laser or laser emitter, external to the nephroscope 100, can generate the laser light. The laser light can be coupled into a proximal end of the optical fiber 128 via a suitable connector. The laser light can have a wavelength that corresponds to a spectral peak of absorption of human blood and saline, such as 2100 nm, 1942 nm, and others. For example, wavelengths in the range between 1900 nm and 3000 nm can correspond to a spectral region in which water is absorbing, while wavelengths between 400 nm and 520 nm can correspond to a spectral region in which oxy-hemoglobin and/or deoxy-hemoglobin is absorbing. For example, a thulium fiber laser can produce laser light at a wavelength of 1908 nm or 1940 nm, a thulium:YAG laser can produce laser light at a wavelength of 2010 nm, a holmium:YAG laser can produce laser light at a wavelength of 2120 nm, and an erbium:YAG laser can produce laser light at a wavelength of 2940 nm. Other wavelengths in these ranges can also be used. In general, delivering laser light that has significant absorption in blood and saline can be beneficial, because such laser light can be minimally invasive on surrounding tissue, which can reduce or eliminate damage to the tissue at or near the kidney stone. The laser can provide light having an output power that falls within a suitable range of output power, such as between 20 watts and 120 watts, between about 20 watts and about 120 watts, and others. These ranges of output power are mere examples, and other suitable output powers or ranges of output power can also be used. The optical fiber 128 can be a multi-mode fiber or a single-mode fiber.

A laser controller 132 (see FIG. 2) can be located on the grippable proximal portion 104 of the body 102. The laser controller 132 can toggle a state of the laser light between an operational state ("on") and a non-operational state ("off"). For example, the laser controller 132 can direct a wired and/or wireless signal to a laser that is located external to the nephroscope 100. The signal can turn on or turn off the laser. In some implementations, the practitioner can adjust one or more settings of the laser, such as the output power, on a housing of the laser. In some implementations, the practitioner can adjust one or more settings of the laser via the laser controller 132.

During a typical procedure, the practitioner can manipulate the laser controller 132 such that the laser can be operational for a period of time, such as one minutes, two minutes, three minutes, four minutes, or any suitable length of time. During the period of time of laser operation, the practitioner can manipulate the body 102 to move the delivered laser light across a surface of the kidney stone. In some examples, the laser power level and the exposure times are such that the practitioner can safely switch the laser power on and off by hand, without a need for a mechanized or automated exposure mechanism. The laser power may also be low enough such that incidental exposure of surrounding tissue may not damage the tissue.

The practitioner can ablate the kidney stone by performing what is referred to as dusting of the surface of the kidney stone. Dusting can wear down the kidney stone in a controlled manner, and can produce kidney stone particles that can be smaller than kidney stone fragments obtained from fragmenting or fracturing the kidney stone. For example, a typical kidney stone can be sized between about 1 mm and about 20 mm. Fragmenting or fracturing the kidney stone can produce kidney stone fragments that can be sized smaller than the size of the stone, such as between a few mm and less than about 10 mm in size. Dusting of the kidney stone can produce kidney stone particles that can be smaller than about 1 mm in size.

To remove the kidney stone fragments, the practitioner can use a stone retrieval device, such as a basket, that can pass through an orifice in the nephroscope 100. The practitioner can use the stone retrieval device to select and remove individual fragments. In addition to, or instead of, the stone retrieval device, the nephroscope 100 can include a flushing system to flush away the stone fragments.

The nephroscope 100 can include a flushing system at the distal end 110 of the body 102. The flushing system can controllably deliver a flow of an irrigation agent, such as a saline solution, to the ablation site and can controllably remove the irrigation agent and the kidney stone fragments from the ablation site.

The flushing system can include an irrigation lumen 134 (see FIG. 4) that extends along the body 102 to the distal end 110 of the body 102. The irrigation lumen 134 can deliver an irrigation fluid to the kidney stone and the kidney stone fragments. A proximal end of the irrigation lumen 134 can connect, via a suitable connector, to a suitable irrigation fluid source (e.g., a pump that can transport irrigation fluid from an irrigation fluid reservoir).

The flushing system can also include a suction lumen 136 (see FIG. 4) that extends along the body 102 to the distal end 110 of the body 102. The suction lumen 136 can remove the irrigation fluid and the kidney stone fragments from the kidney. A proximal end of the suction lumen 136 can connect, via a suitable connector, to a suitable suction or vacuum source that can suitably dispose of the irrigation agent and the kidney stone fragments.

The flushing system can include a flushing controller 138 (see FIG. 2) located on the grippable proximal portion 104 of the body 102. The flushing controller 138 can control a flow of irrigation fluid through the irrigation lumen 134 and suction in the suction lumen 136. The flushing controller 138 can include a depressible flushing control button that, when depressed repeatedly, cycles through one or more irrigation levels and/or suction levels, before turning off the irrigation and suction. For example, sequentially depressing the flushing control button can cause the irrigation and suction to switch from off to a lowest level, then from the lowest level to an intermediate level, then from the intermediate level to a highest level, then from the highest level to off, the from off to the lowest level, and so forth. The flushing controller 138 can control the irrigation and suction, together, with a single control. Other suitable flushing control elements can also be used, such as a positionable slide, a positionable lever, or a positionable dial that can specify an irrigation level and/or a suction level. The flushing controller 138 can select from one of a plurality of specified discrete irrigation/suction levels. The flushing controller 138 can specify the irrigation/suction level in a continuous (e.g., a non-discrete) manner.

The nephroscope 100 can optionally include a tube, chamber, additional working channel, or other passage 140 within a body of the nephroscope 100. A practitioner can use the passage 140 to deploy a separate tool or instrument, such as a lithotripter, a stone retrieval basket, or another suitable tool or instrument.

In some implementations, the entire nephroscope 100 can be disposed after a single use. In some implementations, one or more elements of the nephroscope 100 can be disposable, while one or more elements of the nephroscope 100 can be reused for later procedures. For example, the elongated rigid portion 106 and the flexible distal portion 108 can be detachable from (and/or reattachable to) the grippable proximal portion 104, so that the grippable proximal portion 104 can be cleaned and/or sterilized and reused, while the elongated rigid portion 106 and the flexible distal portion 108 can be discarded after a single use. As another example, the flexible distal portion 108 can be detachable from the elongated rigid portion 106, so that the grippable proximal portion 104 and the elongated rigid portion 106 can be cleaned and/or sterilized and reused, while the flexible distal portion 108 can be discarded after a single use.

Figure 7:
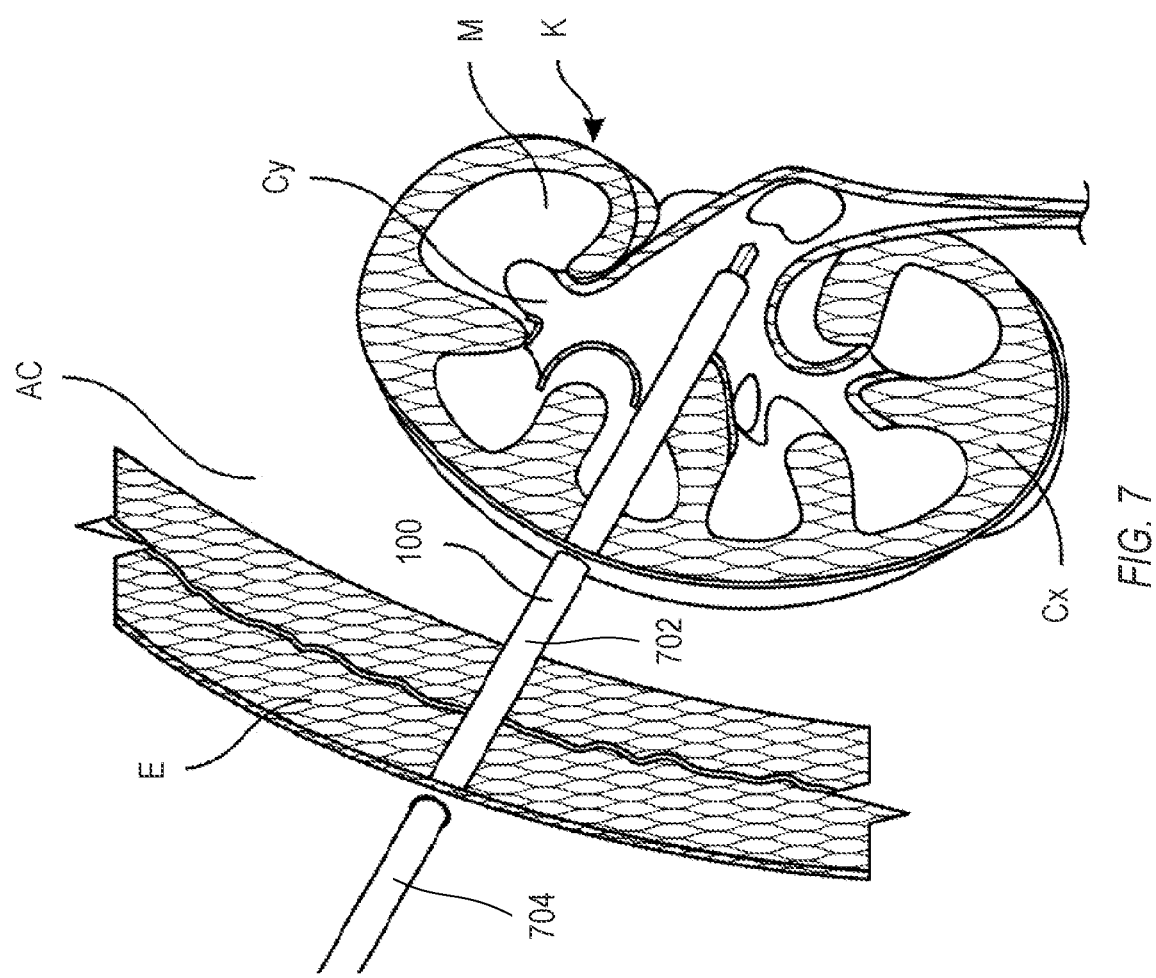
FIG. 7 is a schematic illustration of a kidney in an abdominal cavity, taken in a coronal plane.

FIG. 7 is a schematic illustration of kidney K in abdominal cavity AC taken in a coronal plane. Abdominal cavity AC can be defined by epidermal layers E that provide a barrier to access of kidney K. The nephroscope 100 can be inserted through epidermal layers E and into kidney K. Kidney K can comprise outer cortex Cx, medulla M and calyces Cy. Kidney stones can form in kidney K in various places, particularly in calyces Cy.

During use, the practitioner can insert the flexible distal portion 108 partially or fully into the body of the patient, and specifically into the kidney of the patient. During use, a distal portion 702 of the elongated rigid portion 106 can be located inside the body of the patient, while a proximal portion 704 of the elongated rigid portion 106 can remain outside the body of the patient. The grippable proximal portion 104 of the body 102 remains outside the patient's body before, during, and after use of the nephroscope 100. The grippable proximal portion 104 of the body 102 can be shaped to be grippable by a human hand.

Figure 8:
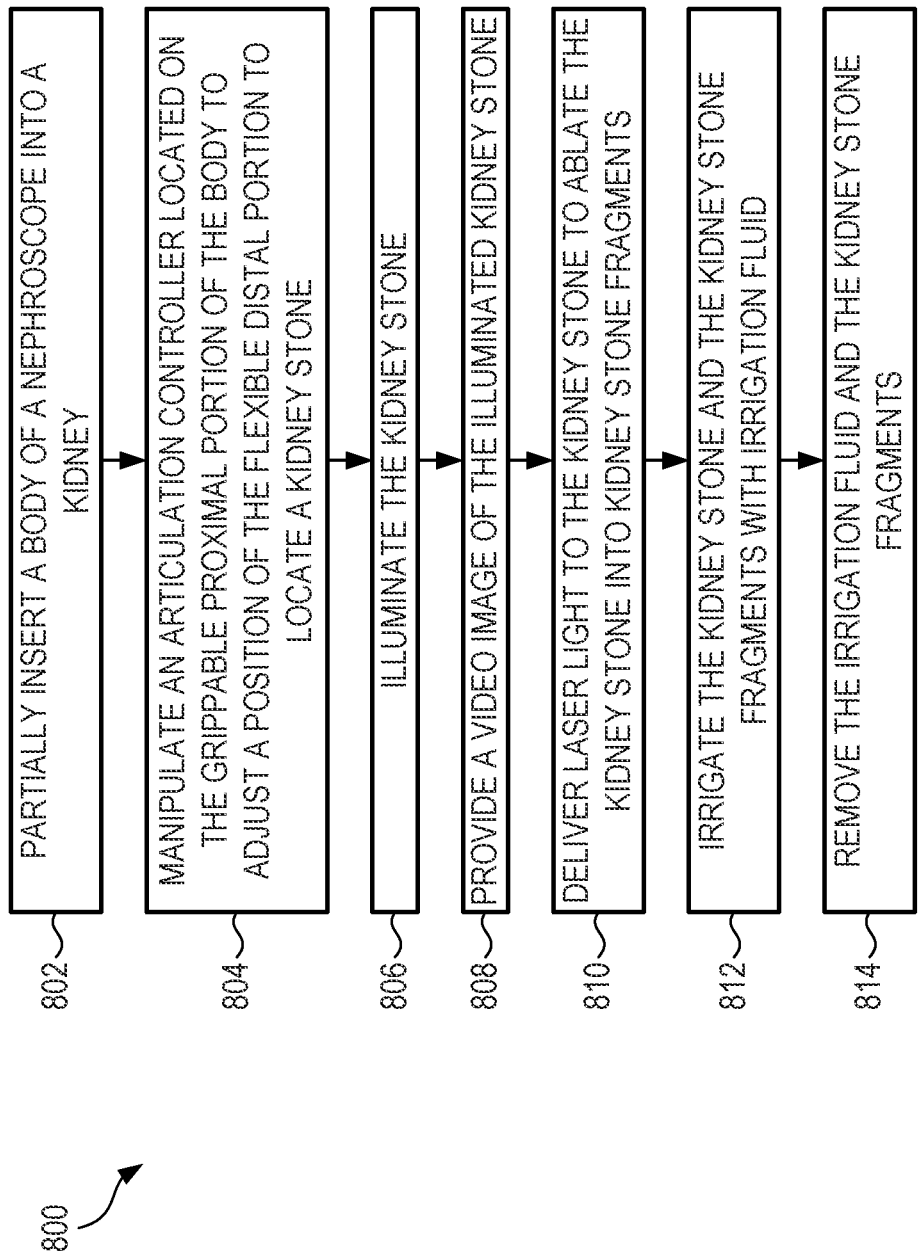
FIG. 8 shows a flow chart of a method for operating a nephroscope.

FIG. 8 shows a flow chart of an example of a method 800 for operating a nephroscope. The method 800 can be executed on the nephroscope 100 of FIGS. 1-5, or on other suitable nephroscopes. The method 800 is but one example of a method for operating a nephroscope. Other suitable methods can also be used.

At operation 802, a practitioner can partially insert a body of a nephroscope into a kidney of a patient. The body can include a grippable proximal portion, an elongated rigid portion extending from the grippable proximal portion, and a flexible distal portion extending distally from the elongated rigid portion to a distal end.

At operation 804, the practitioner can manipulate an articulation controller located on the grippable proximal portion of the body to adjust a position of the flexible distal portion to locate a kidney stone, while the body is inserted into the kidney of the patient.

At operation 806, the practitioner can, with the distal end of the body, illuminate the kidney stone.

At operation 808, the practitioner can, with the distal end of the body, provide a video image of the illuminated kidney stone.

At optional operation 810, the practitioner can, with the distal end of the body, deliver laser light to the kidney stone to ablate the kidney stone into kidney stone fragments.

At optional operation 812, the practitioner can, with the distal end of the body, irrigate the kidney stone and the kidney stone fragments with irrigation fluid.

At optional operation 814, the practitioner can, with the distal end of the body, remove the irrigation fluid and the kidney stone fragments.

Figure 9:
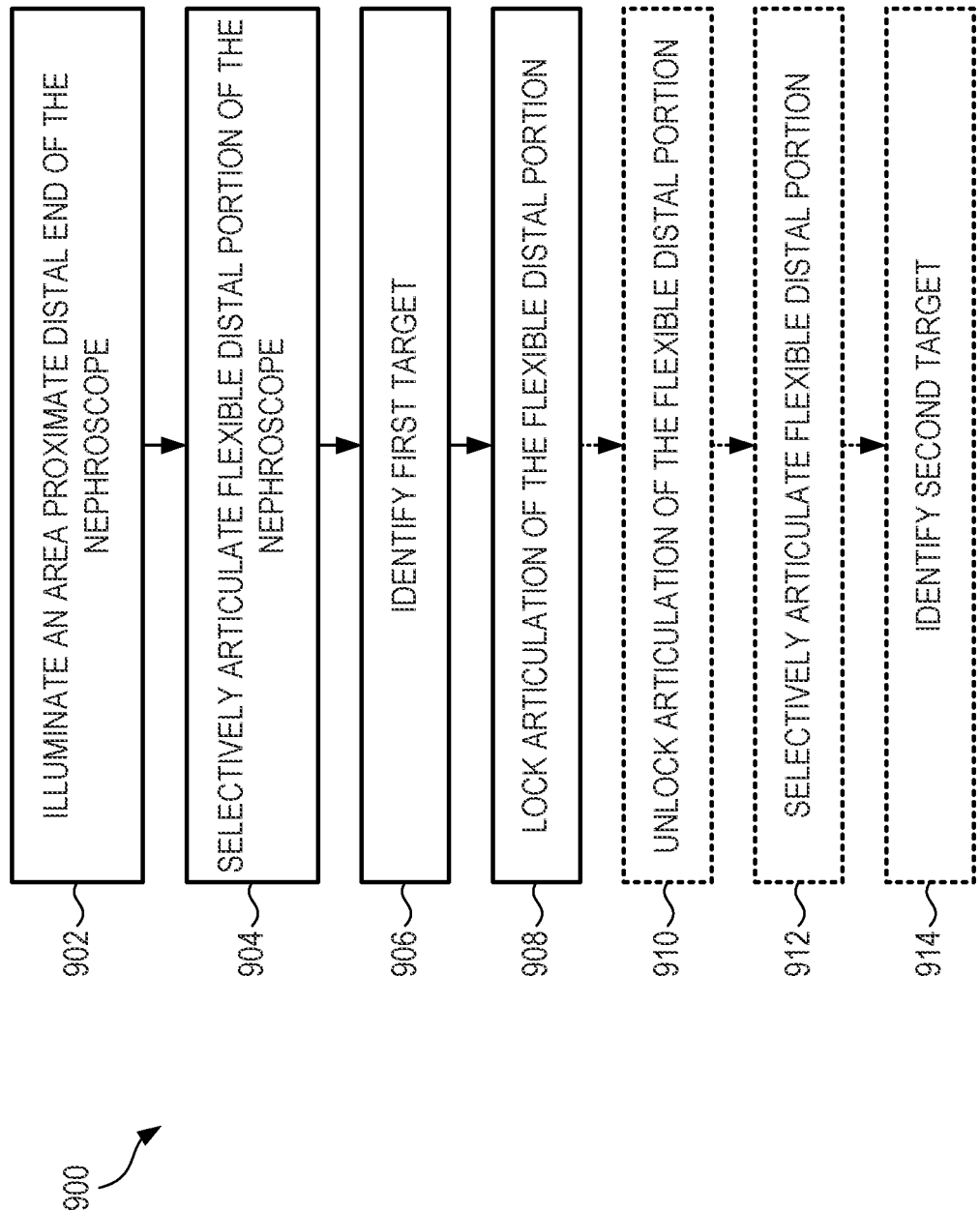
FIG. 9 shows a flow chart of an example of a method for imaging using a nephroscope.

FIG. 9 shows a flow chart of an example of a method 900 for imaging using a nephroscope. The method 900 can be executed on the nephroscope 100 of FIGS. 1-5, or on other suitable nephroscopes. The method 900 is but one example of a method for imaging using a nephroscope. Other suitable methods can also be used.

At operation 902, a practitioner can use the nephroscope to illuminate, with a distal end of the nephroscope, an area proximate the distal end of the nephroscope.

At operation 904, the practitioner can use the nephroscope to selectively articulate a flexible distal portion of the nephroscope to adjust a position of the distal end of the nephroscope to locate a first target.

At operation 906, the practitioner can use the nephroscope to identify, from an image of the illuminated area when the distal end of the nephroscope is at a first position, the first target in the area proximate the distal end of the nephroscope.

At operation 908, the practitioner can use the nephroscope to lock articulation of the flexible distal portion of the nephroscope to fixedly position the distal end of the nephroscope at the first position.

At optional operation 910, the practitioner can use the nephroscope to unlock the articulation of the flexible distal portion of the nephroscope.

At optional operation 912, the practitioner can use the nephroscope to selectively articulate the flexible distal portion of the nephroscope to adjust a position of the distal end of the nephroscope to locate a second target.

At optional operation 914, the practitioner can use the nephroscope to identify, from an image of the illuminated area when the distal end of the nephroscope is at a second position, the second target in the area proximate the distal end of the nephroscope.

EXAMPLES

To further illustrate the device, related system, and/or related method discussed herein, a non-limiting list of examples is provided below. Each of the following non-limiting examples can stand on its own or can be combined in any permutation or combination with any one or more of the other examples.

In Example 1, a nephroscope can include: a body at least partially insertable into a kidney of a patient, the body including a grippable proximal portion, an elongated rigid portion extending from the grippable proximal portion, and a flexible distal portion extending distally from the elongated rigid portion to a distal end; and an articulation controller on the grippable proximal portion of the body and configured to adjust a position of the flexible distal portion to locate a kidney stone when the body is inserted into the kidney of the patient, the distal end of the body being further configured to illuminate the kidney stone, provide a video image of the illuminated kidney stone, ablate the kidney stone, and remove kidney stone fragments.

In Example 2, the nephroscope of Example 1 can optionally be configured such that: the articulation controller is coupled to a plurality of pull wires that extend along the body to the flexible distal portion; the pull wires are located at a respective plurality of angular locations on the body and on the flexible distal portion; and the articulation controller is configured to adjust the position of the flexible distal portion by controllably applying a proximally oriented force to a first pull wire, of the plurality of pull wires, at a first angular location to cause the flexible distal portion of the body to move radially in the direction of the first angular location.

In Example 3, the nephroscope of any one of Examples 1-2 can optionally be configured such that: the grippable proximal portion of the body is shaped to be grippable by a human hand; and the articulation controller is located to be actuatable by a thumb of the human hand when the human hand grips the grippable proximal portion of the body.

In Example 4, the nephroscope of any one of Examples 1-3 can optionally be configured such that the distal end of the body includes: a substrate located on the distal end of the body; at least one light-emitting diode located on the substrate and configured to emit light distally away from the distal end of the body to illuminate the kidney stone; and a camera located on the substrate and configured to capture the video image of the illuminated kidney stone.

In Example 5, the nephroscope of any one of Examples 1-4 can optionally be configured such that: the at least one light-emitting diode includes two light-emitting diodes; and the camera is located between the two light-emitting diodes.

In Example 6, the nephroscope of any one of Examples 1-5 can optionally be configured such that the circuit board is configured to produce a digital video signal representing the captured video image of the illuminated kidney stone.

In Example 7, the nephroscope of any one of Examples 1-6 can optionally further include an electrical port on the body coupled to the circuit board, the electrical port configured to receive electrical power to power the circuit board and provide a wired connection to the digital video signal.

In Example 8, the nephroscope of any one of Examples 1-7 can optionally further include a display coupled to the grippable proximal portion of the body and configured to display the captured video image of the illuminated kidney stone.

In Example 9, the nephroscope of any one of Examples 1-8 can optionally further include an optical fiber extending along a working channel in the body to the distal end of the body, the optical fiber configured to deliver laser light to the kidney stone to ablate the kidney stone into the kidney stone fragments.

In Example 10, the nephroscope of any one of Examples 1-9 can optionally be configured such that the laser light has a wavelength that corresponds to a spectral peak of absorption of human blood and saline.

In Example 11, the nephroscope of any one of Examples 1-10 can optionally be configured such that the laser light has a wavelength of 2100 nm.

In Example 12, the nephroscope of any one of Examples 1-11 can optionally further include a laser controller located on the grippable proximal portion of the body and configured to toggle a state of the laser light between an operational state and a non-operational state.

In Example 13, the nephroscope of any one of Examples 1-12 can optionally further include: an irrigation lumen extending along the body to the distal end of the body, the irrigation lumen configured to deliver an irrigation fluid to the kidney stone and the kidney stone fragments; and a suction lumen extending along the body to the distal end of the body, the suction lumen configured to remove the irrigation fluid and the kidney stone fragments from the kidney.

In Example 14, the nephroscope of any one of Examples 1-13 can optionally further include: a flushing controller located on the grippable proximal portion of the body and configured to control a flow of irrigation fluid through the irrigation lumen and suction in the suction lumen.

In Example 15, the nephroscope of any one of Examples 1-14 can optionally be configured such that the flushing controller comprises a depressible flushing control button that, when depressed repeatedly, cycles through one or more irrigation levels before turning off the irrigation and suction.

In Example 16, a nephroscope can include: a body partially insertable into a kidney of a patient, the body including a grippable proximal portion, an elongated rigid portion extending from the grippable proximal portion, and a flexible distal portion extending distally from the elongated rigid portion to a distal end; and an articulation controller located on the grippable proximal portion of the body and configured to adjust a position of the flexible distal portion to locate a kidney stone when the body is inserted into the kidney of the patient, the distal end of the body being further configured to illuminate the kidney stone, provide a video image of the illuminated kidney stone, deliver laser light to the kidney stone to ablate the kidney stone into kidney stone fragments, irrigate the kidney stone and the kidney stone fragments with irrigation fluid, and remove the irrigation fluid and the kidney stone fragments.

In Example 17, the nephroscope of Example 16 can optionally be configured such that: the articulation controller is coupled to a plurality of pull wires that extend along the body to the flexible distal portion; the pull wires are located at a respective plurality of angular locations on the body and on the flexible distal portion; and the articulation controller is configured to adjust the position of the flexible distal portion by controllably applying a proximally oriented force to a first pull wire, of the plurality of pull wires, at a first angular location to cause the flexible distal portion of the body to move radially in the direction of the first angular location.

In Example 18, the nephroscope of any one of Examples 16-17 can optionally be configured such that the distal end of the body includes: a circuit board on the distal end of the body; at least one light-emitting diode on the circuit board and configured to emit light distally away from the distal end of the body to illuminate the kidney stone; and a camera on the circuit board and configured to capture the video image of the illuminated kidney stone.

In Example 19, a nephroscope can include: a body partially insertable into a kidney of a patient, the body including a grippable proximal portion, an elongated rigid portion extending from the grippable proximal portion, and a flexible distal portion extending distally from the elongated rigid portion to a distal end; a plurality of pull wires that extend along the body to the flexible distal portion, the pull wires being located at a respective plurality of angular locations on the body and on the flexible distal portion; an articulation controller located on the grippable proximal portion of the body and configured to adjust the position of the flexible distal portion by controllably applying a proximally oriented force to a first pull wire, of the plurality of pull wires, at a first angular location to cause the flexible distal portion of the body to move radially in the direction of the first angular location, the plurality of pull wires and the articulation controller configured to adjust a position of the flexible distal portion to locate a kidney stone when the body is inserted into the kidney of the patient; a circuit board located on the distal end of the body; at least one light-emitting diode on the circuit board and configured to emit light distally away from the distal end of the body to illuminate the kidney stone; a camera on the circuit board and configured to capture a video image of the illuminated kidney stone; an optical fiber extending along a working channel in the body to the distal end of the body, the optical fiber configured to deliver laser light to the kidney stone to ablate the kidney stone into kidney stone fragments; an irrigation lumen extending along the body to the distal end of the body, the irrigation lumen configured to deliver an irrigation fluid to the kidney stone and the kidney stone fragments; and a suction lumen extending along the body to the distal end of the body, the suction lumen configured to remove the irrigation fluid and the kidney stone fragments from the kidney.

In Example 20, the nephroscope of Example 19 can optionally further include a display coupled to the grippable proximal portion of the body and configured to display the captured video image of the illuminated kidney stone.

In Example 21, the nephroscope of any one of Examples 1-20 can optionally be configured such that the articulation controller is further configured to removably lock the position of the flexible distal portion, with respect to the grippable proximal portion, at a selectable position.

In Example 22, the nephroscope of any one of Examples 1-21 can optionally be configured such that the articulation controller is further configured to switch between a first configuration, in which the position of the flexible distal portion is adjustable, and a second configuration, in which the position of the flexible distal portion is lockable at a selectable position.

In Example 23, the nephroscope of any one of Examples 1-21 can optionally be configured such that the articulation controller is further configured to releasably lock the position of the flexible distal portion by locking a position of each of the plurality of pull wires.

In Example 24, a method for imaging using a nephroscope can include: illuminating, with a distal end of the nephroscope, an area proximate the distal end of the nephroscope; selectively articulating a flexible distal portion of the nephroscope to adjust a position of the distal end of the nephroscope to locate a first target; identifying, from an image of the illuminated area when the distal end of the nephroscope is at a first position, the first target in the area proximate the distal end of the nephroscope; and locking articulation of the flexible distal portion of the nephroscope to fixedly position the distal end of the nephroscope at the first position.

In Example 25, the method of Example 24 can optionally be configured such that: selectively articulating the flexible distal portion comprises selectively articulating the flexible distal portion with an articulation controller located on a proximal portion of the nephroscope; locking articulation of the flexible distal portion comprises locking the articulation with the articulation controller; and fixedly positioning the distal end of the nephroscope at the first position comprises fixedly positioning, with respect to the proximal portion of the nephroscope, the distal end of the nephroscope at the first position.

In Example 26, the method of any one of Examples 24-25 can optionally further include: unlocking the articulation of the flexible distal portion of the nephroscope; selectively articulating the flexible distal portion of the nephroscope to adjust a position of the distal end of the nephroscope to locate a second target; and identifying, from an image of the illuminated area when the distal end of the nephroscope is at a second position, the second target in the area proximate the distal end of the nephroscope.

What is claimed is:
1. A nephroscope, comprising:
a body at least partially insertable into a kidney of a patient, the body including a grippable proximal portion, an elongated rigid portion extending from the grippable proximal portion, and a flexible distal portion extending distally from the elongated rigid portion to a distal end;
an articulation controller on the grippable proximal portion of the body and configured to adjust a position of the flexible distal portion to locate a kidney stone when the body is inserted into the kidney of the patient;

a plurality of pull wires connected to the articulation controller to adjust the position of the flexible distal portion;

a laser controller located on the grippable proximal portion of the body and configured to toggle a state of a laser light between an operational state and a non-operational state;

an optical fiber extending within the elongated rigid portion to the flexible distal portion, the optical fiber configured to deliver the laser light toggled by the laser controller;

an irrigation lumen extending along the body to the distal end of the body; and a suction lumen extending along the body to the distal end of the body;

wherein the distal end of the body is further configured to illuminate the kidney stone, provide a video image of the illuminated kidney stone, ablate the kidney stone, and remove kidney stone fragments.

2. The nephroscope of claim 1, wherein the articulation controller is further configured to removably lock the position of the flexible distal portion, with respect to the grippable proximal portion, at a selectable position.

3. The nephroscope of claim 1, wherein the articulation controller is further configured to switch between a first configuration, in which the position of the flexible distal portion is adjustable, and a second configuration, in which the position of the flexible distal portion is lockable at a selectable position.

4. The nephroscope of claim 1, wherein:
the plurality of pull wires are located at a respective plurality of angular locations on the body and on the flexible distal portion; and
the articulation controller is configured to adjust the position of the flexible distal portion by controllably applying a proximally oriented force to a first pull wire, of the plurality of pull wires, at a first angular location to cause the flexible distal portion of the body to move radially in the direction of the first angular location.

5. The nephroscope of claim 4, wherein the articulation controller is further configured to releasably lock the position of the flexible distal portion by locking a position of each of the plurality of pull wires.

6. The nephroscope of claim 1, further comprising a circuit board that includes:
at least one light-emitting diode located on the circuit board and configured to emit light distally away from the distal end of the body to illuminate the kidney stone; and
a camera located on the circuit board and configured to capture the video image of the illuminated kidney stone.

7. The nephroscope of claim 6, wherein:
the at least one light-emitting diode includes two light-emitting diodes; and
the camera is located between the two light-emitting diodes.

8. The nephroscope of claim 6, wherein the circuit board is configured to produce a digital video signal representing the captured video image of the illuminated kidney stone; and
further comprising an electrical port on the body coupled to the circuit board, the electrical port configured to receive electrical power to power the circuit board and provide a wired connection to the digital video signal.

9. The nephroscope of claim 6, further comprising a display coupled to the grippable proximal portion of the body and configured to display the captured video image of the illuminated kidney stone.

10. The nephroscope of claim 1, wherein the optical fiber extends along a working channel in the body to the distal end of the body, the optical fiber configured to deliver the laser light to the kidney stone to ablate the kidney stone into the kidney stone fragments, wherein the laser light has a wavelength that corresponds to a spectral peak of absorption of human blood and saline.

11. The nephroscope of claim 1, wherein
the irrigation lumen is configured to deliver an irrigation fluid to the kidney stone and the kidney stone fragments; and
the suction lumen is configured to remove the irrigation fluid and the kidney stone fragments from the kidney.

12. The nephroscope of claim 11, further comprising:
a flushing controller located on the grippable proximal portion of the body and configured to control a flow of irrigation fluid through the irrigation lumen and suction in the suction lumen.

13. The nephroscope of claim 12, wherein the flushing controller comprises a depressible flushing control button that, when depressed repeatedly, cycles through one or more irrigation levels before turning off the irrigation and suction.

14. The nephroscope of claim 1, wherein the articulation controller is switchable between a first state, in which the elongated rigid portion and the flexible distal portion have a similar rigidity, and a second state, in which the flexible distal portion is less rigid than the elongated rigid portion.

15. The nephroscope of claim 1, wherein the flexible distal portion is constructed with at least one of a braid or a mesh.

16. The nephroscope of claim 1, wherein the elongated rigid portion extending from the grippable proximal portion defines a first length, and the flexible distal portion extending distally from the elongated rigid portion to the distal end defines a second length that is less than the first length.

17. A nephroscope, comprising:
a body partially insertable into a kidney of a patient, the body including a grippable proximal portion, an elongated rigid portion extending from the grippable proximal portion, and a flexible distal portion extending distally from the elongated rigid portion to a distal end;
a plurality of pull wires that extend along the body to the flexible distal portion, the pull wires being located at a respective plurality of angular locations on the body and on the flexible distal portion;
an articulation controller located on the grippable proximal portion of the body and configured to adjust the position of the flexible distal portion by controllably applying a proximally oriented force to a first pull wire, of the plurality of pull wires, at a first angular location to cause the flexible distal portion of the body to move radially in the direction of the first angular location, the plurality of pull wires and the articulation controller configured to adjust a position of the flexible distal portion to locate a kidney stone when the body is inserted into the kidney of the patient;
a laser controller located on the grippable proximal portion of the body and configured to toggle a state of a laser light between an operational state and a non-operational state;
a circuit board located on the distal end of the body;
the grippable proximal portion of the body shaped to be grippable by a human hand;

the articulation controller located to be actuatable by a thumb of the human hand when the human hand grips the grippable proximal portion of the body;

the laser controller located to be actuatable by a finger of the human hand when the human hand grips the grippable proximal portion of the body;

at least one light-emitting diode on the circuit board and configured to emit light distally away from the distal end of the body to illuminate the kidney stone;

a camera on the circuit board and configured to capture a video image of the illuminated kidney stone;

an optical fiber extending along a working channel in the body to the distal end of the body, the optical fiber configured to deliver laser light to the kidney stone to ablate the kidney stone into kidney stone fragments;

an irrigation lumen extending along the body to the distal end of the body, the irrigation lumen configured to deliver an irrigation fluid to the kidney stone and the kidney stone fragments; and a suction lumen extending along the body to the distal end of the body, the suction lumen configured to remove the irrigation fluid and the kidney stone fragments from the kidney.

18. The nephroscope of claim 17, wherein the articulation controller is further configured to switch between a first configuration, in which the position of the flexible distal portion is adjustable, and a second configuration, in which the position of the flexible distal portion is lockable at a selectable position.

* * * * *